(12) United States Patent
Hoyme et al.

(10) Patent No.: US 9,259,586 B2
(45) Date of Patent: Feb. 16, 2016

(54) SYSTEMS AND METHODS FOR HIGHLY SAFE ADJUSTMENT OF DEVICE PARAMETERS

(75) Inventors: Kenneth P. Hoyme, Plymouth, MN (US); James O. Gilkerson, Stillwater, MN (US); James Kalgren, Lino Lakes, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 744 days.

(21) Appl. No.: 12/559,730

(22) Filed: Sep. 15, 2009

(65) Prior Publication Data

US 2010/0069991 A1 Mar. 18, 2010

Related U.S. Application Data

(60) Provisional application No. 61/097,047, filed on Sep. 15, 2008.

(51) Int. Cl.
*A61N 1/37* (2006.01)
*A61N 1/372* (2006.01)
*G06F 19/00* (2011.01)
*A61N 1/362* (2006.01)

(52) U.S. Cl.
CPC ........ *A61N 1/37247* (2013.01); *A61N 1/37252* (2013.01); *G06F 19/3406* (2013.01); *A61N 1/362* (2013.01); *G06F 19/3437* (2013.01)

(58) Field of Classification Search
CPC ........... A61N 1/37247; A61N 1/37252; G06F 19/3406

USPC .............................................. 607/30–32, 60
See application file for complete search history.

(56) References Cited

U.S. PATENT DOCUMENTS

| 5,345,362 | A | 9/1994 | Winkler |
| 5,716,384 | A * | 2/1998 | Snell .............................. 607/30 |
| 6,497,655 | B1 | 12/2002 | Linberg et al. |
| 6,842,644 | B2 * | 1/2005 | Anderson et al. ............... 607/32 |
| 6,880,085 | B1 | 4/2005 | Balczewski et al. |
| 7,027,872 | B2 | 4/2006 | Thompson |

(Continued)

FOREIGN PATENT DOCUMENTS

| WO | WO2007018566 | 2/2007 |
| WO | WO-2007127596 | 11/2007 |
| WO | 2010031033 | 3/2010 |

OTHER PUBLICATIONS

"Zoom® Latitude® Programming System, Model 3120," Jun. 27, 2007, 52 pages.

(Continued)

*Primary Examiner* — Tammie K Heller
(74) *Attorney, Agent, or Firm* — Pauly, DeVries Smith & Deffner, LLC

(57) ABSTRACT

A system and method of programming a cardiac rhythm management device (CRM device) using an external programming device are described, where the user is presented with a list of highly-safe parameter adjustments. Input is received from the user selecting one or more of the highly-safe parameter adjustments. A programming session is initiated wherein the programming device establishes communication with the CRM device, and transmits the selected one or more highly-safe parameter adjustments to the CRM device.

20 Claims, 7 Drawing Sheets

(56) References Cited

U.S. PATENT DOCUMENTS

| | | | |
|---|---|---|---|
| 7,060,031 | B2 | 6/2006 | Webb et al. |
| 7,191,006 | B2 * | 3/2007 | Hu et al. ............. 607/30 |
| 7,218,968 | B2 | 5/2007 | Condie et al. |
| 7,257,447 | B2 | 8/2007 | Cates et al. |
| 7,272,444 | B2 | 9/2007 | Peterson et al. |
| 2003/0125776 | A1 | 7/2003 | Turney et al. |
| 2004/0088020 | A1 * | 5/2004 | Condie et al. ............. 607/30 |
| 2004/0128161 | A1 | 7/2004 | Mazar et al. |
| 2005/0010258 | A1 | 1/2005 | Peterson et al. |
| 2005/0256550 | A1 | 11/2005 | Gilkerson et al. |
| 2005/0283198 | A1 | 12/2005 | Haubrich et al. |
| 2006/0074465 | A1 | 4/2006 | Webb |
| 2007/0185547 | A1 | 8/2007 | Hoyme et al. |
| 2007/0299317 | A1 | 12/2007 | Hoyme et al. |

OTHER PUBLICATIONS

PCT International Search Report and Written from International Application No. PCT/US2009/056924, corresponding to U.S. Appl. No. 12/559,730 mailed Dec. 29, 2009 (12 pages).

"Japanese Office Action", from JP Application No. 2011527037, mailed Oct. 19, 2012, (pp. 1-9) Including English translation.

"PCT Notification Concerning Transmittal of International Preliminary Report on Patentability", from International Application No.PCT/US2009/056924, corresponding to U.S. Appl. No. 12/559,730, mailed Mar. 24, 2011, pp. 1-7.

"Response to Communication pursuant to Rule 161(2) and Rule 162 EPC", Response to European Written Opinion, dated Jul. 15, 2011, filed Dec. 16, 2011 for EP Patent Application No. 09792533.3-2305, corresponding to U.S. Appl. No. 12/559,730, (pp. 1-12).

"Examination Report", from AU Application No. 2009290594, mailed Jun. 28, 2013, 4 pages.

"First Office Action", for China Application No. 200980136914.8, mailed Mar. 11, 2013 (22 pages).

"Official Action", for Japanese Application No. 2011-527037, mailed May 29, 2013 (4 pages) with English translation.

"Second Office Action", for Chinese Patent Application No. 200980136914.8, mailed Oct. 12, 2013 (23 pages) English translation.

"Third Office Action", for Chinese Patent Application No. 200980136914.8, mailed Mar. 4, 2014 (25 pages) English translation.

"Decision on Rejection", for Chinese Patent Application No. 200980136914.8, mailed Jun. 4, 2014 (35 pages) with English translation.

"Response to Second Examination Report", for Australian Patent Application No. 2009290594, mailed Jul. 30, 2014 and filed with the Australian Patent Office Sep. 29, 2014 (3 pages).

"Second Examiner Report", for Australian Patent Application No. 2009290594, mailed Jul. 30, 2014 (4 pages).

* cited by examiner

SYSTEMS AND METHODS FOR HIGHLY SAFE ADJUSTMENT OF DEVICE PARAMETERS

This application claims the benefit of U.S. Provisional Application No. 61/097,047, filed Sep. 15, 2008, the content of which is herein incorporated by reference.

TECHNICAL FIELD

This disclosure relates generally to medical systems and, more particularly, to medical systems that can be used to communicate with implanted medical devices, amongst other things.

BACKGROUND OF THE INVENTION

Implantable medical devices can be used to provide pacing therapy to patients who have cardiac rhythm problems. For example, an implanted cardiac rhythm management (CRM) device can be used to provide pacing therapy to a patient with sinus node dysfunction, where the heart fails to properly initiate depolarization waves, or an atrio-ventricular conduction disturbance, where the conduction of depolarization waves through the heart tissue is impaired.

Implanted medical devices frequently communicate with devices located outside of the body. For example, an external programming device is capable of two-way communication with the implanted device and can not only receive information from the implanted device, but can also transmit operational parameters to the implanted device, that is, program the device. This type of device is typically used by a physician or other caregiver in a clinical or hospital setting. Improved programming options are desired.

SUMMARY OF THE INVENTION

Embodiments of the invention are related to medical systems and methods that can be used to communicate with and collect information from implanted medical devices, amongst other things.

In one embodiment, a cardiac rhythm management (CRM) system for facilitating highly safe adjustments includes an implantable CRM device and an external programming device. The external programming device includes a communication module adapted to be communicatively coupled to the CRM device and to request information from and receive information from the CRM device during transmission sessions. The external programming device further includes a display device adapted to present a user of the programming device with a list of at least two highly-safe parameter adjustments, where each parameter adjustment on the list includes the parameter title and a maximum quantity of permitted change for the parameter title. The external programming device also includes a user input device adapted to accept input selecting one or more of the list of highly-safe parameter adjustments. The communication module is configured to transmit the one or more highly-safe parameter adjustments to the CRM device.

In another embodiment, a method of programming a cardiac rhythm management device (CRM device) using an external programming device includes the steps of presenting a user of the programming device with a list of highly-safe parameter adjustments, receiving input from the user selecting one or more of the highly-safe parameter adjustments, initiating a programming session wherein the programming device establishes communication with the CRM device, and transmitting the selected one or more highly-safe parameter adjustment to the CRM device.

In yet another embodiment, the CRM system for facilitating highly safe adjustments is configured so that the list of highly-safe parameter adjustments is presented simultaneously on a single screen of the programming device and labeled as highly-safe on the single screen; This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

Figure 1:
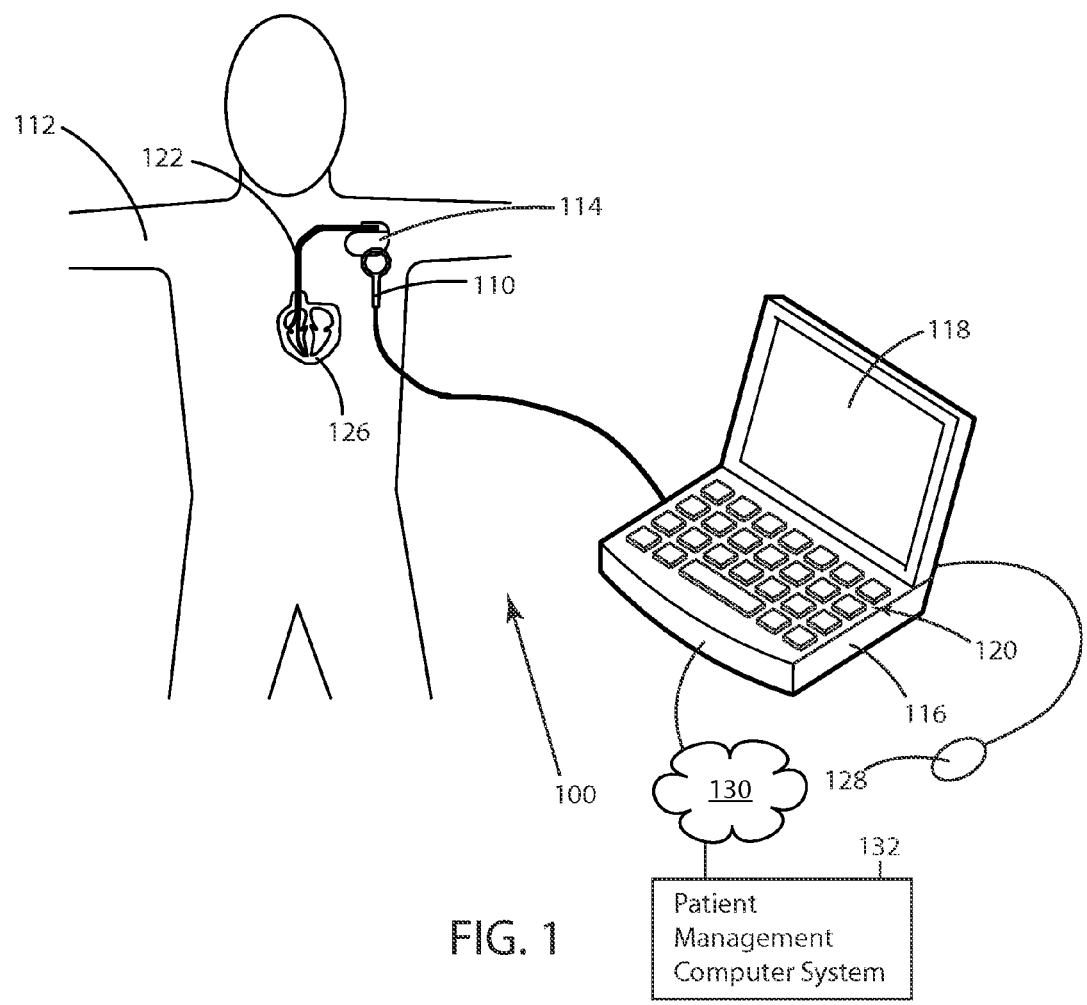
FIG. 1 is a schematic diagram of an exemplary implementation of a cardiac rhythm management (CRM) system, including an implanted CRM device, an external programming device, and a patient management computer system, consistent with at least one embodiment of the invention.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

This disclosure relates generally to medical systems and, more particularly, to medical systems that can be used to communicate with implanted medical devices. In particular, this disclosure relates to the use of external programming devices to communicate with and provide programming parameters for the implanted medical device. Still more specifically, this disclosure relates to a programmer capable of providing highly-safe parameter adjustment options which is particularly useful when programming an implanted medical device remotely and which is also particularly useful when addressing patient concerns.

This invention is directed to systems and methods of facilitating the adjustment of certain device parameters that are highly safe for the patient. Highly safe parameter changes are appropriate for performing when a physician is remote from a patient. Some highly safe parameter changes have a positive impact on the therapy delivered for some patients. In other cases, highly safe parameter changes can have a low chance of truly changing the therapy received by the patient from the implantable medical device.

Physicians are frequently presented with the issue of addressing symptomatic complaints of their patients in the absence of specific data suggesting precisely what will be effective for the specific complaint. In many cases, the patient may not feel that the physician is adequately addressing their concern unless some concrete action is actually taken. In the context of implanted medical devices, this may put the physician in the difficult position of trying to decide what action to take.

In some embodiments, the system described herein can provide physicians with specific settings that can be adjusted to address symptomatic complaints, but that have no downside risk to the patient. In some embodiments, these particular highly-safe settings can be grouped in a specific area of the programmer interface to facilitate their use by the physician. In some embodiments, these highly-safe settings can be suggested by the device in response to the physician inputting the particular symptomatic complaint. The net result of the change could be a positive impact on the patient's perception of the treatment. The physician would benefit as they would be able to provide the patient with peace of mind that they are being listened to and that something is being done in response to their concerns.

One example of a highly safe change is adjusting the maximum tracking rate (MTR) from 125 to 130 beats per minute (bpm). While MTR can be adjusted by increments of 2 in some current systems, this is not currently presented to the physician as a low-risk, highly-safe adjustment that can address patient requests for programming changes. Some current systems check programming parameter changes for safety and unwanted interactions between different parameter settings after they have been entered by the clinician. However, the inventors are not aware of a system that identifies which parameter changes are highly-safe and are not aware of a system where a list of highly-safe parameter change options are presented to the clinician.

A highly-safe parameter adjustment is an adjustment of a previously-programmed parameter by a small increment. In other words, turning on or off a new programming option is not a highly-safe parameter change. But, if a programming option is already activated, then adjusting one of that programming option's parameters by a small amount may be a highly-safe parameter change. The exact amount of the small parameter change will vary depending on the parameter. But generally, changes of a parameter value of 1% or less compared to its current value are highly safe. For example, the following changes could be offered as highly safe programming options:

1) Changing Lower Rate Limit by +/−5 beats per minute (bpm), where a nominal value is 60 bpm.

2) Changing Tachy Zone Rate Limit by +/−5 bpm, where a nominal value is 160 bpm.

3) Changing Post-Ventricular Atrial Refractory Period (PVARP) by +/−5 milliseconds (msec), where a nominal value is between 240 and 280 msec.

4) Changing paced Atrioventricular Delay (paced AV-Delay) by +/−5 msec, where a nominal value for paced AV delay is 180 msec.

5) Changing sensed Atrioventricular Delay (sensed AV-Delay) by +/−5 msec., where a nominal value for sensed AV delay is 120 msec.

5) Changing Atrial Tachy Response (ATR) rate by +/−5 bpm.

6) Changing Maximum Sensor Rate by +/−5 bpm, where a nominal value is 130 bpm.

7) Changing Maximum Tracking Rate by +/−5 bpm, where a nominal value is 130 bpm.

The nominal value mentioned above is the pre-programmed value for a particular parameter in one or more typical CRM devices. If a clinician does not change a parameter value, it will remain at the nominal value after implantation and activation in a patient. The highly-safe parameter changes listed above will be allowed from the current settings for a particular patient, even if the current settings are different from the nominal settings. However, a parameter change that moves a parameter value toward a nominal value is generally considered safer than a parameter change that moves a parameter value away from a nominal value.

In one embodiment, the CRM system uses its knowledge of the patient to generate the list of highly-safe programming options. Further detailed embodiments will now be described with respect to the attached FIGS.

One embodiment of a CRM system will now be described with reference to FIG. 1. In this example, the programmer of an implantable medical device is in the same location as the patient. Another example of a CRM system will be described herein with reference to FIG. 2 where the programmer is remote from the patient. FIG. 1 is a schematic of an exemplary CRM system 100, consistent with at least one embodiment of the invention. The system 100 can include an implantable medical device 114 disposed within a patient 112. The implantable medical device 114 can include pacing functionality. The implantable medical device 114 can be of various types such as, for example, a pacemaker, a cardioverter-defibrillator, a cardiac resynchronization device, or the like. In some embodiments, the implantable medical device 114 can include one or more leads 122 disposed in or near the patient's heart 126.

The implantable medical device 114 can include one or more implantable sensors in order to gather data regarding the patient 112. For example, the implantable medical device 114 can include an activity level sensor, a respiration sensor, a blood pressure sensor, or other sensors.

The implantable medical device 114 can be configured to store data over a period of time, and periodically communicate with the external programming device 116 in order to transmit some or all of the stored data.

The implantable medical device 114 can be in communication with an external programming device 116. In some embodiments, communication between the implantable medical device 114 and the external programming device 116 can be via inductive communication through a wand 110 held on the outside of the patient 112 near the implantable medical device 114. However, in other embodiments, communication can be carried out via radiofrequency transmission, acoustically, or the like.

The external programming system 116 can be for example, a programmer, a programmer/recorder/monitor device, a computer, an advanced patient management system, a personal digital assistant (PDA), or the like. As used herein, the term programmer refers to a device that programs implanted devices, records data from implanted devices, and allows monitoring of the implanted device. Exemplary programmer/recorder/monitor devices include the Model 3120 Programmer, available from Boston Scientific Corporation, Natick, Mass. The external programming device 116 can include a user input device, such as a keyboard 120 and/or a mouse 128. The external programming device 116 can include a video output channel and video output device, such as a video display 118 for displaying video output. The displayed video output can include a user interface screen. In addition, the video display 118 can also be equipped with a touch screen, making it into a user input device as well.

The external programming device 116 can display real-time data and/or stored data graphically, such as in charts or graphs, and textually through the user interface screen. In addition, the external interface device 116 can present a programming menu question to a user along with several response options. The external programming device 116 can also input and store a user's response to the various programming prompts.

In one embodiment, the external programming device 116 is in communication with a patient management computer system 132. The communication link between the external programming device 116 and the patient management computer system 132 may be via phone lines, the Internet 130, or any other data connection. In another embodiment, the external programming device 116 is not in direct communication with a patient management system.

The external programming device 116 is capable of changing the operational parameters of the CRM device 114, and is therefore referred to as a programmer. Typically, programmers are used to interface with CRM devices in a clinic or hospital setting. In this context, the user of the external programming device is a clinician, physician or trained technician.

Figure 2:
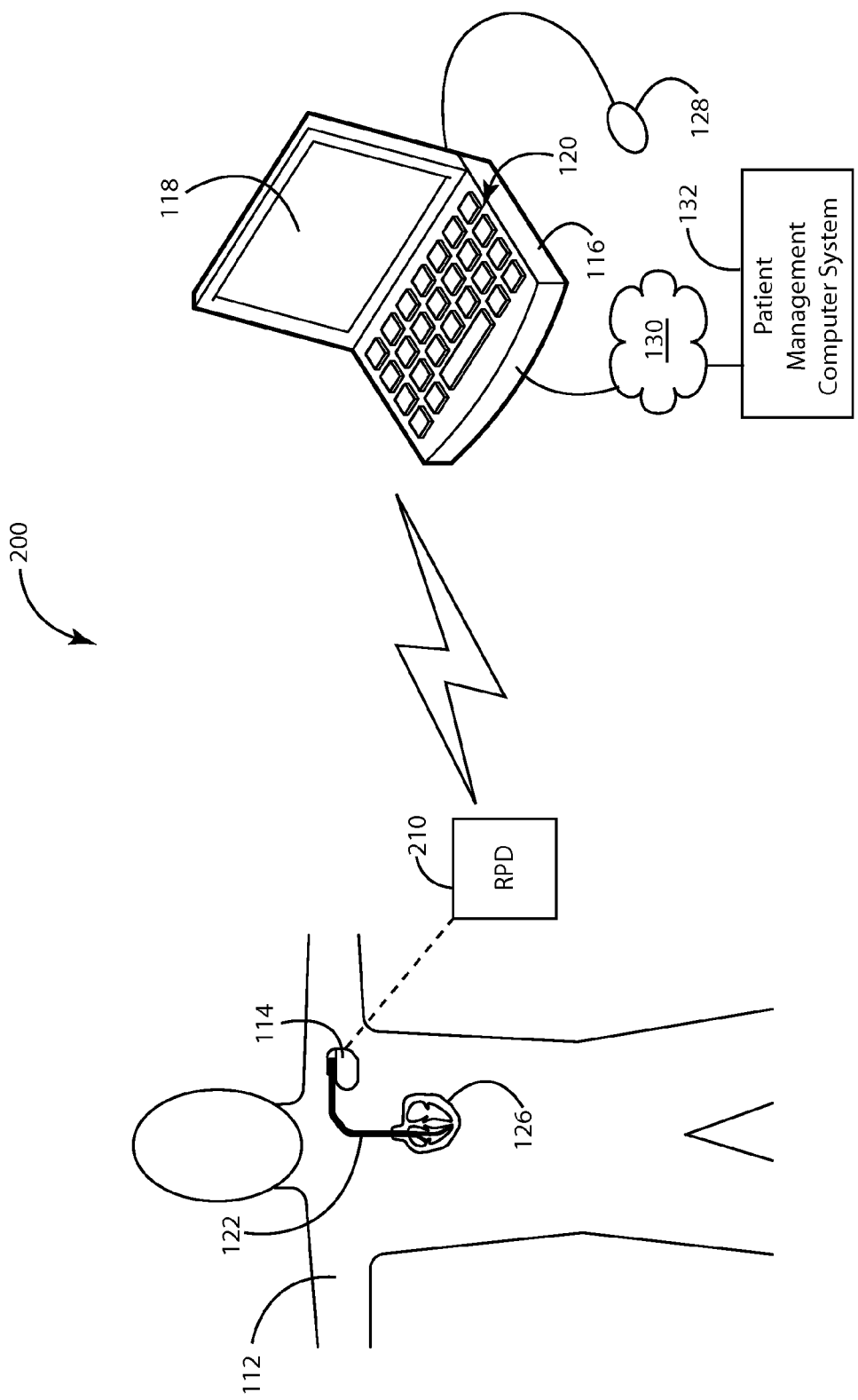
FIG. 2 is a schematic diagram of an exemplary implementation of a cardiac rhythm management (CRM) system where the external programming device is remote from the patient having the implanted CRM device.

Now referring to FIG. 2, a CRM system 200 is illustrated which is designed for use when the programmer and the patient are in different locations, so that the programmer is remote from the patient and not physically present in the same space as the patient. For example, the patient may be at his or her home while the clinician is at a hospital which a few miles away or hundreds of miles away. Like reference numbers across the different FIGS. indicate like elements. In CRM system 200, a remote programming device 210 is in the patient's location and establishes communication with the implantable medical device 114. Communication between the remote programming device 210 and the implantable medical device 114 can be carried out by radiofrequency transmission, acoustically or by inductive communication using a wand held on the outside of the patient 112 near the device 114.

The remote programming device 210 is in communication with an external programming device 116. The communication link between the external programming device 116 and the remote programming device 210 may be via phone lines, the Internet, or any other data connection. Other details of the external programming device 116 and the implantable medical device are similar to as described with respect to FIG. 2.

Further details, options and configurations for systems for remotely programming an implantable medical device are described in co-pending published application titled "System and Method for Remotely Programming a Patient Medical Device," having Publication No. 2007/0185547, which is incorporated by reference herein in its entirety.

Figure 3:
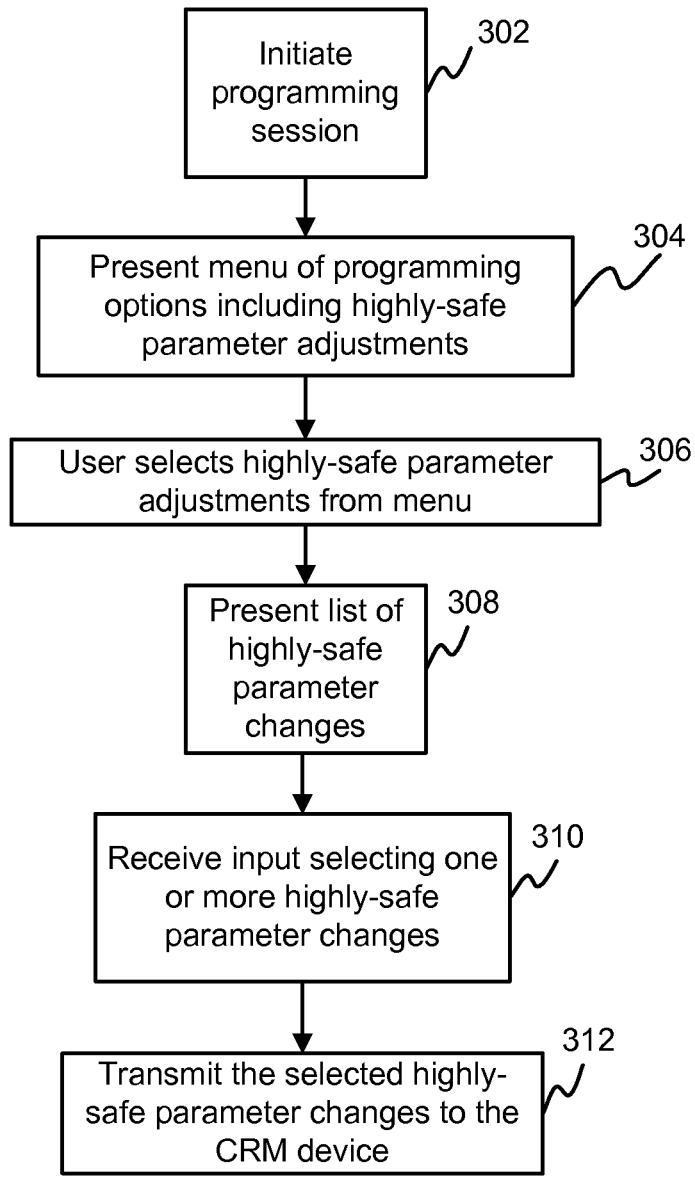
FIG. 3 is a flowchart showing one embodiment of a method of selecting highly-safe parameter information.

One method of programming an implantable medical device with highly-safe parameter changes will now be described with reference to FIG. 3. A transmission session is initiated at step 302 between an implantable or implanted medical device and an external programming device. The user may be presented with a menu of programming options in one embodiment at step 304, where one of those options is highly-safe parameter adjustments. If the user selects highly-safe parameter adjustments at step 306, then the user is presented with a list of highly-safe parameter changes at step 308.

Steps 304 and 306 are optional, and it is also possible that the user is presented with a list of highly-safe parameter changes without having to select that option from a menu. For example, if the programming session is taking place remotely, the external programming device can be configured to recognize that the session is remote, and as a result, only present the highly-safe parameter adjustments to the user at step 308. The presentation of the list to the user can be accomplished on the display device 118 of the external programming device 116 shown in FIGS. 1 and 2.

Referring back to FIG. 3, next, the external programming device receives input selecting one or more of the highly-safe parameter adjustments at step 310. The user can provide input by using a keyboard or a mouse to check a box next to one of the parameter changes on the list, or in any number of other ways. Next, the highly-safe parameter change is transmitted to the implantable medical device at step 312.

Figure 4:
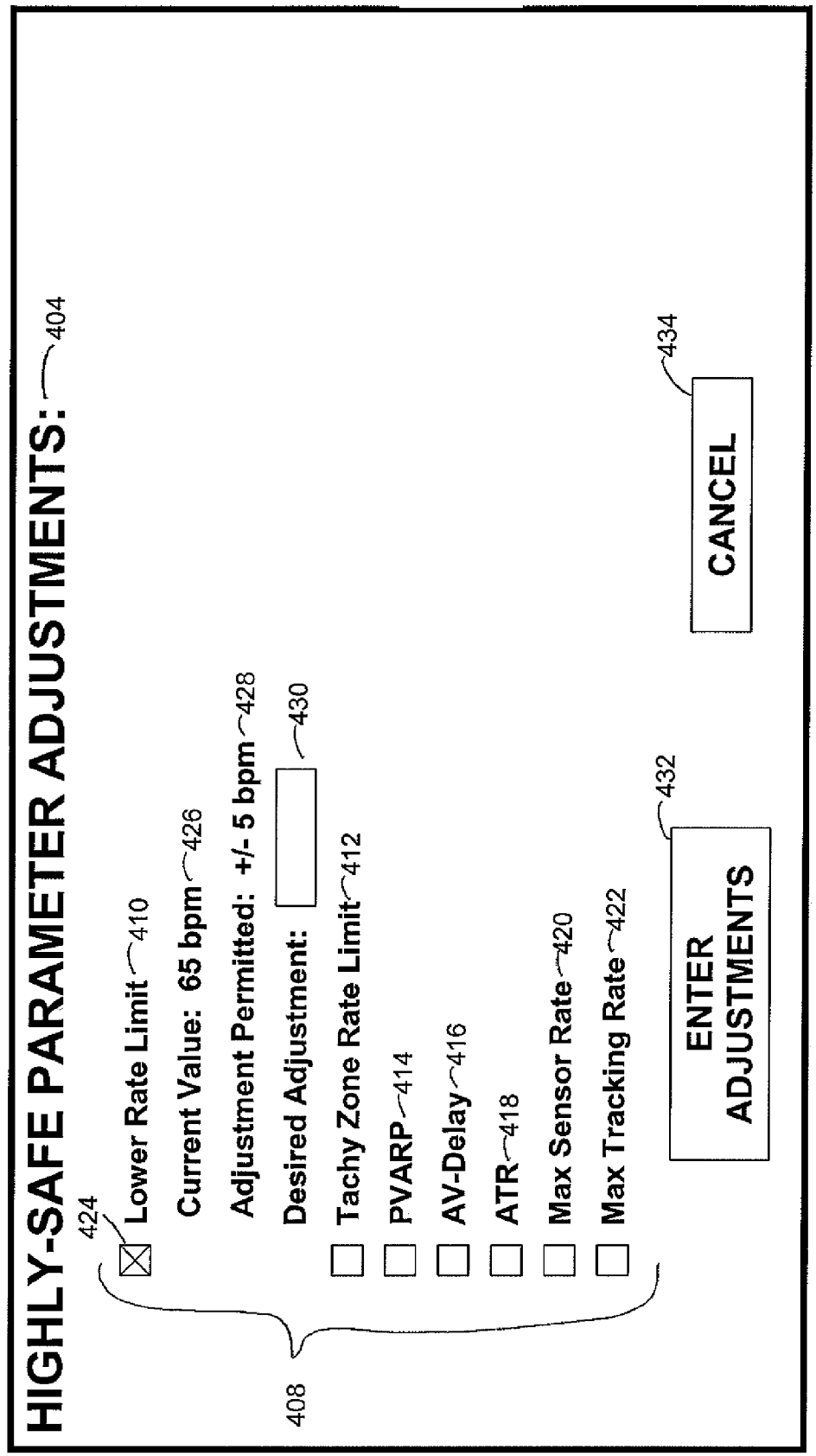
FIG. 4 is one embodiment of a prompt for a display device for collecting event information.

Now referring to FIG. 4, an example screen shot 400 of one embodiment is shown for presenting the highly-safe parameter adjustments to the user. The screen includes a title 404 indicating that the list is one of highly-safe parameter adjustments. The screen 400 also includes a list 408 of highly safe parameter adjustments 410, 412, 414, 416, 418, 420 and 422. Each of the highly-safe parameter adjustments has a checkbox 424 corresponding to it. If the checkbox is checked by a user for a particular adjustment, then additional details are shown related to that parameter. For example, in FIG. 4, the parameter adjustment 410 for "Lower Rate Limit" has been checked. As a result, the current value 426 of 65 beats per minute (bpm) is shown, the range of permissible adjustment 428 of plus or minus 5 bpm is shown, and a field 430 is provided for the user to enter the desired adjustment to the lower rate limit.

It is also possible to customize the list of highly safe parameter options based on many different types of patient specific information. One example of patient specific information is an indication that is present for a particular patient. In this document, an "indication" includes a symptom or particular circumstance that indicates the advisability or necessity of a specific medical treatment or procedure. An "indication for use of an implantable medical device" or "device indication" includes a symptom or particular circumstance that indicates the advisability or necessity of one or more specific medical treatments that are deliverable by an implantable medical device or one or more specific medical procedures that are performable by the implantable medical device.

Commonly-owned U.S. Pat. No. 7,257,447 discusses an indication-based programming method and programming device for an implantable medical device. The programming device collects patient-specific information including a patient's indications for use of the implantable medical device and automatically produces values for operational parameters enabling the implantable medical device to deliver one or more therapies according to the indications.

In addition to indications, the patient-specific information includes, but is not limited to, the patient's demographic data, cardiac history, electrogram, electrocardiogram (ECG), echocardiogram (indicative of ejection fraction, for example), physical attributes, non-cardiac disease history, and/or drug regimens. Further examples of such patient-specific information and an example of a system for determining patient-specific parameters for programming an implantable medical device are discussed in published patent application U.S. 2005/0256550, entitled "Method and apparatus for question-based programming of cardiac rhythm management devices," filed on May 13, 2004, assigned to Cardiac Pacemakers, Inc., which is incorporated herein by reference in its entirety. The patient-specific information allows for optimization of therapy delivery for each individual patient. The values for the operational parameters produced by the programming device are then used to program the implantable medical device via telemetry. Thus, the programming device substantially automates the process between the diagnosis of the patient's indications and other conditions and the programming of the implantable medical device. The indication-based programming allows a user, such as a physician or other caregiver, to optimally utilize features and capabilities of an implantable medical device based on the patient's specific conditions.

Figure 5:
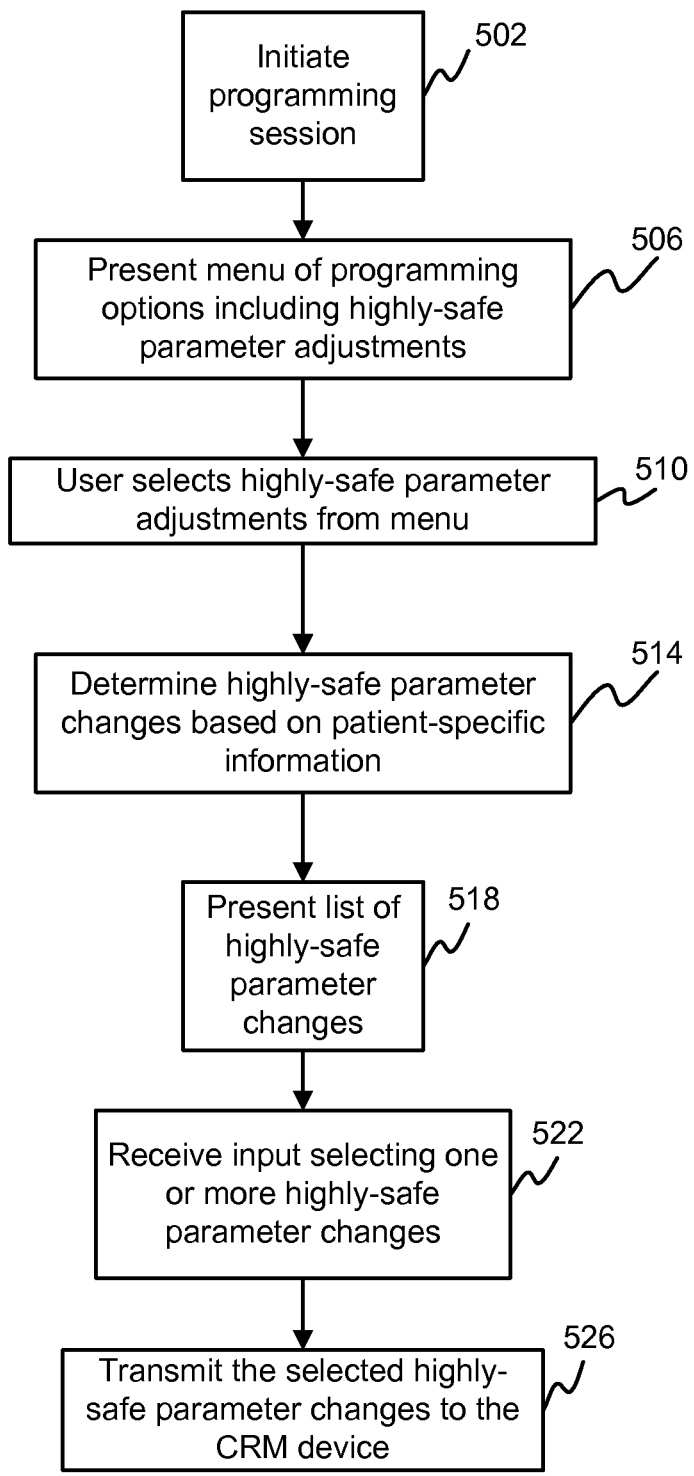
FIG. 5 is another flowchart showing a different embodiment of a method of selecting highly-safe parameter information.

FIG. 5 is a flowchart of another method of programming an implantable medical device with highly-safe parameter changes. A transmission session is initiated at step 502 between an implantable or implanted medical device and an external programming device. The user is presented with a menu of programming options in one embodiment at step 506, where one of those options is highly-safe parameter adjustments. If the user selects highly-safe parameter adjustments at step 510, then the system draws on the patient-specific information that is available and determines a list of highly-safe parameter changes at step 514.

The list of possible highly-safe parameter changes mentioned previously herein are candidates for inclusion, but some may be eliminated or modified based on the patient-specific information. For example, if the patient is known to have chronic atrial fibrillation then the system will not offer a change in the AV delay parameter. The system could, however, offer a larger range of adjustments to the ATR rate, such as +/−10 bpm.

In another example, if the patient is known to have normal PR intervals during cardiac cycles, then the system might allow larger ranges of AV delay adjustment. The system could offer adjustments to the paced AV delay parameter of +/−10 msec. However, for a patient with third degree heart block or a patient with heart failure, the highly-safe parameters adjustments to paced AV delay will be limited to +/−5 msec.

Once the system has determined a list of highly-safe parameter changes based on patient-specific information, and then the user is presented with the list at step 518. Steps 506 and 510 are optional, and it is instead possible that the user is presented with a list of highly-safe parameter changes without having to select that option from a menu. For example, if the programming session is taking place remotely, the external programming device can be configured to recognize that the session is remote, and as a result, only present the highly-safe parameter adjustments to the user at step 518. The presentation of the list to the user can be accomplished on the display device 118 of the external programming device 116 shown in FIGS. 1 and 2.

Referring back to FIG. 5, next, the external programming device receives input selecting one or more of the highly-safe parameter adjustments at step 522. The user can provide input by using a keyboard or a mouse to check a box next to one of the parameter changes on the list, or in any number of other ways. Next, the highly-safe parameter change is transmitted to the implantable medical device at step 526.

It is also possible for patient-specific information to be input by the user during the programming session, such as by inputting a description of the patient's symptoms. For example, the user can be prompted to input a patient concern that has not been satisfied by other programming changes.

The user can be provided with a list of common concerns with checkboxes for being checked by the user, such as a concern that the device is not turned on, a complaint that the device is beeping or making other noises, or another concern that is difficult to address. In response to this input, the CRM system can select one of the highly-safe parameter changes, and can indicate to the user that a highly-safe parameter change has been made.

Figure 6:
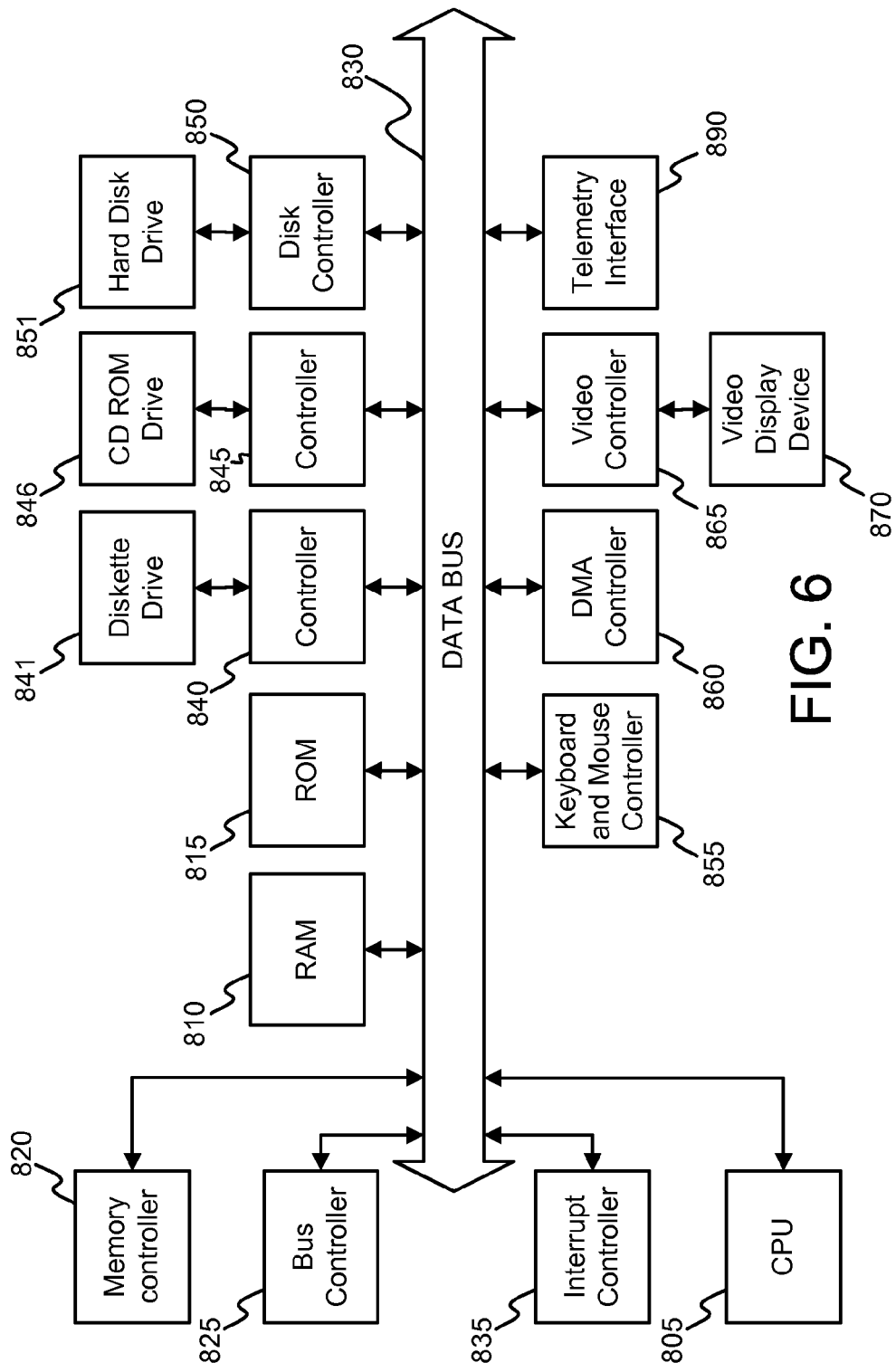
FIG. 6 is a schematic diagram of an implementation of the components of an external programming device, in accordance with various embodiments.

External programming devices can include components common to many computing devices. Referring now to FIG. 6, a diagram of various components is shown in accordance with some embodiments of the invention. However, it is not required that an external programming device have all of the components illustrated in FIG. 6.

In one embodiment, the external programming device includes a central processing unit (CPU) 805 or processor, which may include a conventional microprocessor, random access memory (RAM) 810 for temporary storage of information, and read only memory (ROM) 815 for permanent storage of information. A memory controller 820 is provided for controlling system RAM 810. A bus controller 825 is provided for controlling data bus 830, and an interrupt controller 835 is used for receiving and processing various interrupt signals from the other system components.

Mass storage can be provided by diskette drive 841, which is connected to bus 830 by controller 840, CD-ROM drive 846, which is connected to bus 830 by controller 845, and hard disk drive 851, which is connected to bus 830 by controller 850. User input to the programmer system may be provided by a number of devices. For example, a keyboard and mouse can connected to bus 830 by keyboard and mouse controller 855. DMA controller 860 is provided for performing direct memory access to system RAM 810. A visual display is generated by a video controller 865 or video output, which controls video display 870. The external system can also include a telemetry interface 890 or telemetry circuit which allows the external system to interface and exchange data with an implantable medical device. It will be appreciated that some embodiments may lack various elements illustrated in FIG. 6.

Figure 7:
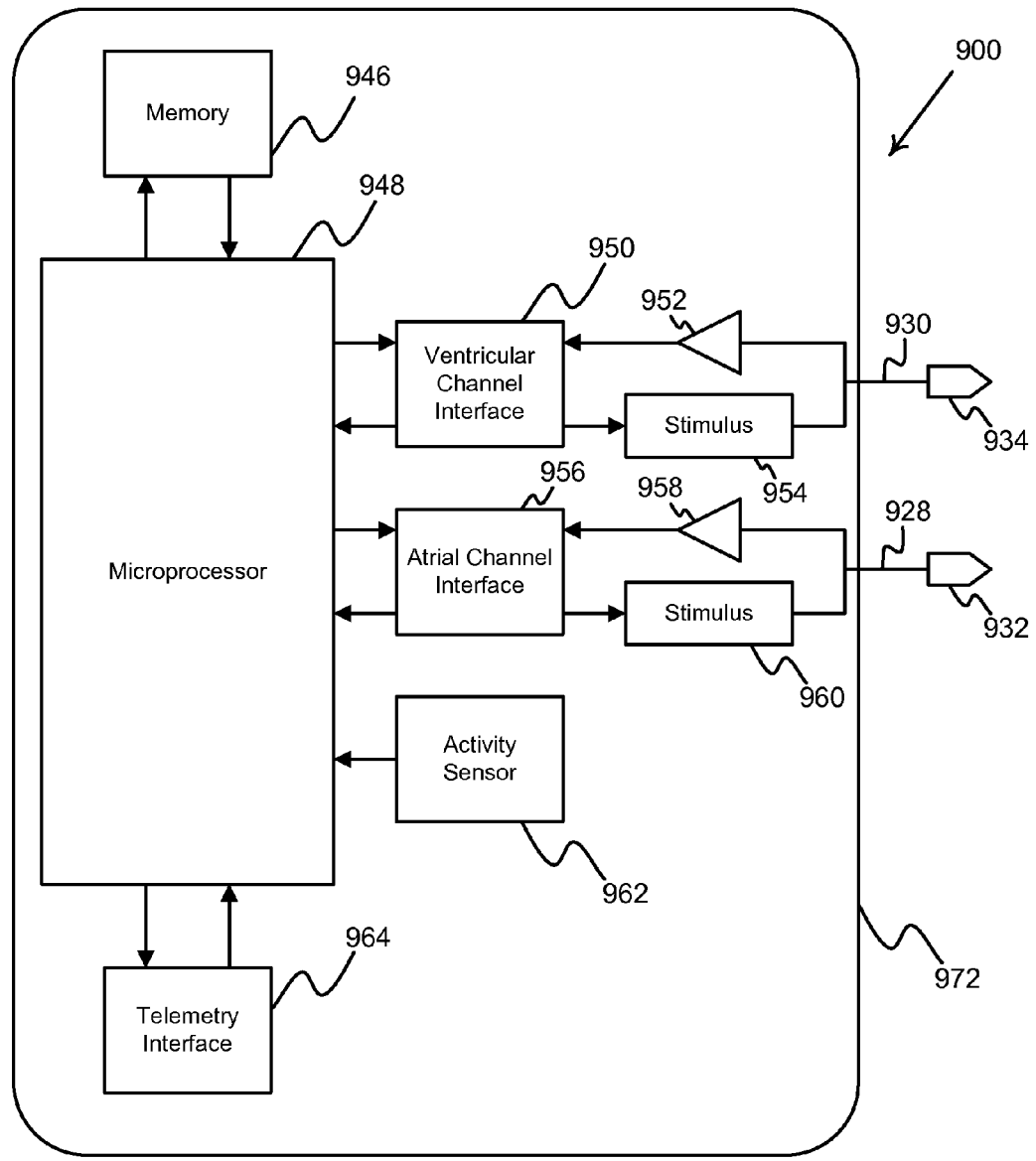
FIG. 7 is a schematic view of components of an implantable medical system in accordance with an embodiment of the invention.

Referring now to FIG. 7, some components of an exemplary implantable system 900, such as an implantable CRM device, are schematically illustrated. The implantable medical system 900 can include an implantable medical device 972 coupled to one or more stimulation leads 930 and 928. The implantable device 972 can also include other sensors such as activity sensor 962.

The implantable device can include a microprocessor 948 (or processor) that communicates with a memory 946 via a bidirectional data bus. The memory 946 typically comprises ROM or RAM for program storage and RAM for data storage. The implantable device can be configured to execute various operations such as processing of signals and execution of methods as described herein. A telemetry interface 964 is also provided for communicating with an external unit, such as a programmer device or a patient management system.

The implantable device can include ventricular sensing and pacing channels comprising sensing amplifier 952, output circuit 954, and a ventricular channel interface 950 which communicates bidirectionally with a port of microprocessor 948. The ventricular sensing and pacing channel can be in communication with stimulation lead 930 and electrode 934. The implantable device can include atrial sensing and pacing channels comprising sensing amplifier 958, output circuit 960, and an atrial channel interface 956 which communicates bidirectionally with a port of microprocessor 948. The atrial sensing and pacing channel can be in communication with stimulation lead 928 and electrode 932. For each channel, the same lead and electrode can be used for both sensing and pacing. The channel interfaces 950 and 956 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A cardiac rhythm management (CRM) system for facilitating highly safe adjustments, comprising:
   an implantable CRM device having parameters with current values;
   an external programming device comprising:
   i. a communication module adapted to be communicatively coupled to the CRM device and to request information from and receive information from the CRM device during transmission sessions;
   ii. a display device configured to display programming options for the implantable CRM device; and
   iii. a user input device adapted to accept input selecting one or more highly-safe parameter adjustments from a list of highly-safe parameter adjustments;
   wherein the communication module is configured to transmit the one or more highly-safe parameter adjustments to the CRM device, and the external programming device is configured to limit the programming options displayed on the display device to the list of highly-safe parameter adjustments, wherein each highly-safe parameter adjustment has a parameter title and a maximum quantity of permitted change for the parameter adjustment that is no more than 1% compared to the parameter's current value.

2. The system of claim 1 wherein the display device is adapted to present the list of highly-safe parameter adjustments simultaneously on a single screen of the programming device.

3. The system of claim 2 wherein the display device is adapted to label the list of highly-safe parameter adjustments as highly-safe on the single screen.

4. The system of claim 1 wherein the list of highly-safe parameter adjustments is determined in part based on patient-specific information.

5. The system of claim 1 wherein the user input device is further configured to receive user input that describes patient-specific information, wherein the external programming device uses the patient-specific information to determine the list of highly-safe parameter adjustments.

6. The system of claim 1 wherein the external programming device is configured to identify whether or not the programming device is in a different location than a patient in which the CRM device is implanted.

7. The system of claim 6 wherein if the programming device is in a different location than the patient, then the external programming device will only present the user with parameter adjustment options that are highly-safe parameter adjustments.

8. The system of claim 1 wherein the external programming device is a remote external programming device which will only present the user with parameter adjustment options that are highly-safe parameter adjustment options.

9. A method of programming a cardiac rhythm management device (CRM device) using an external programming device, comprising the steps of:
   presenting a user of the programming device with a list of highly-safe parameter adjustments on a programmer interface, wherein the highly-safe parameter adjustments are grouped in a specific area on the programmer interface, and are identified as highly-safe, and are a maximum change of 1% of a current parameter value;
   receiving input from the user selecting one or more of the highly-safe parameter adjustments;
   initiating a programming session wherein the programming device establishes communication with the CRM device; and
   transmitting the selected one or more highly-safe parameter adjustments to the CRM device.

10. The method of claim 9 wherein the user is presented with a list of at least two highly-safe parameter adjustments simultaneously on a single screen of the programming device.

11. The method of claim 10 wherein the step of presenting further comprises labeling the list of highly-safe parameter adjustments as highly-safe on the single screen.

12. The method of claim 9 wherein the list of highly-safe parameter adjustments is determined in part based on patient-specific information.

13. The method of claim 9 further comprising:
    receiving user input that describes a patient's symptom; and
    in response to the user input that describes patient's symptoms, presenting the user with the list of highly-safe parameter adjustments.

14. The method of claim 9 further comprising the step of identifying whether or not the programming device is in a different location than a patient in which the CRM device is implanted.

15. The method of claim 14 wherein if the programming device is in a different location than the patient, then the external programming device will only present the user with parameter adjustment options that are highly-safe parameter adjustments.

16. The method of claim 9 wherein the external programming device is configured for remote external programming and will only present the user with parameter adjustment options that are highly-safe parameter adjustment options.

17. A cardiac rhythm management (CRM) system for facilitating highly safe adjustments, comprising:
   an implantable CRM device having parameters with current values;
   an external programming device that is in a location that is remote from a location of the implantable CRM device, comprising:
   iv. a communication module adapted to be communicatively coupled to the CRM device and to request information from and receive information from the CRM device during transmission sessions,
   v. a display device adapted to display programming options for the implantable CRM device;
   vi. a central processing unit adapted to limit the programming options displayed on the display device to a list of at least two highly-safe parameter adjustments, wherein each parameter adjustment on the list has a parameter title and a maximum quantity of permitted change for the parameter adjustment that is no more than 1% of the parameter's current value, wherein the list is presented simultaneously on a single screen of the programming device and labeled as highly-safe on the single screen; and
   vii. a user input device adapted to accept input selecting one or more of the highly-safe parameter adjustments from the list of highly-safe parameter adjustments;
   wherein the communication module is configured to transmit the one or more highly-safe parameter adjustments to the CRM device.

18. The system of claim 17 wherein the list of highly-safe parameter adjustments is determined in part based on patient-specific information.

19. The system of claim 17 wherein the external programming device is configured to identify whether or not the programming device is in a different location than a patient in which the CRM device is implanted, wherein if the programming device is in a different location than the patient, then the external programming device will only present the user with parameter adjustment options that are highly-safe parameter adjustments.

20. The system of claim 17 wherein the external programming device is configured for remote external programming and will only present the user with parameter adjustment options that are highly-safe parameter adjustment options.

* * * * *